(12) United States Patent
Jaspers et al.

(10) Patent No.: US 6,737,509 B1
(45) Date of Patent: May 18, 2004

(54) ZINSI POLYPEPTIDE COMPOSITION STIMULATING PANCREATIC ISLET GROWTH

(75) Inventors: Stephen R. Jaspers, Edmonds, WA (US); Katherine H. Sprugel, Seattle, WA (US); Hong Ping Ren, Kirkland, WA (US); Jacqueline M. Humes, Seattle, WA (US); Ross C. Hoffman, San Diego, CA (US); Darrell C. Conklin, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/518,842

(22) Filed: Mar. 3, 2000

Related U.S. Application Data

(62) Division of application No. 08/991,890, filed on Dec. 16, 1997, now Pat. No. 6,114,307.
(60) Provisional application No. 60/033,003, filed on Dec. 16, 1996.

(51) Int. Cl.$^7$ ................... C07K 1/00; C07K 14/62; C07H 21/04; A61K 38/28
(52) U.S. Cl. ............. 530/350; 530/303; 530/351; 530/399; 514/2; 514/3; 514/12; 435/69.1; 435/70.1; 536/23.5
(58) Field of Search ................ 435/69.1, 70.1; 512/2, 3, 12; 530/300, 303, 350, 399; 424/85.1, 184.1, 198.1

(56) References Cited

U.S. PATENT DOCUMENTS 5,910,480 A * 6/1999 Koman et al. ............. 514/12

FOREIGN PATENT DOCUMENTS

WO   97/16549   5/1997

OTHER PUBLICATIONS

Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Chassin et al. Cloning of a new member of the insulin gene superfamily (INSL4) expressed in human placenta. Genomics 29: 465–470, 1995.*
Bellet et al. Identification of pro–EPIL and EPIL peptides translated from insulin–like 4 (INSL4) mRNA in human placenta. J Clin Endocrinol Metab 82: 3169–3172, 1997.*
Koman et al., *J. Biol. Chem.* 271: 20238–20241, 1996.
Hillier et al., WashU–Merck EST Project, Accession No. H02449, 1995.
Hillier et al., WashU–Merck EST Project, Accession No. R16073, 1995.
Hillier et al., WashU–Merck EST Project, Accession No. R31278, 1995.
Hillier et al., WashU–Merck EST Project, Accession No. R31794, 1995.
Hillier et al., WashU–Merck EST Project, Accession No. R62136, 1995.
Hillier et al., WashU–Merck EST Project, Accession No. R62240, 1995.
Hillier et al., WashU–Merck EST Project, Accession No. R67799, 1995.
Hillier et al., WashU–Merck EST Project, Accession No. R68426, 1995.
Hillier et al., WashU–Merck EST Project, Accession No. R77100, 1995.
Hillier et al., WashU–Merck EST Project, Accession No. R75651, 1995.
illier et al., WashU–Merck EST Project, Accession No. R77804, 1995.
Hillier et al., WashU–Merck EST Project, Accession No. H02448, 1995.

* cited by examiner

*Primary Examiner*—Gary Kunz
*Assistant Examiner*—Bridget E. Bunner
(74) *Attorney, Agent, or Firm*—Shelby J. Walker

(57) ABSTRACT

The present invention provides compositions for stimulating an increase in islet proliferation and β-cell mass using an insulin homolog polypeptide. The present invention also includes methods for treating diabetes by stimulating islet proliferation and β-cell mass increases and affecting insulin levels.

3 Claims, 2 Drawing Sheets

US 6,737,509 B1

ZINSI POLYPEPTIDE COMPOSITION STIMULATING PANCREATIC ISLET GROWTH

REFERENCE TO RELATED APPLICATIONS

This application is a divisional of U.S. patent application Ser. No. 08/991,890, filed Dec. 16, 1997, now U.S. Pat. No. 6,114,307, issued on Sep. 5, 2000, which is related to U.S. Provisional Patent Application Serial No. 60/033,003, filed on Dec. 16, 1996. Under 35 U.S.C §§ 119(e)(1) and 120, this application claims benefit of said applications and patent.

BACKGROUND OF THE INVENTION

β-cells are specialized cells that secrete insulin and are found in pancreatic islets. Insulin belongs to a group of protein/polypeptide hormones. Insulin increases the rate of synthesis of glycogen, fatty acids, and proteins and stimulates glycolysis and cell proliferation. It also promotes the transport of glucose, and some other sugars, and amino acids into muscle and fat cells. Insulin levels are regulated to maintain glycemic homeostasis, and an important mechanism for regulating insulin production, and hence insulin levels, is β-cell mass.

During the lifetime of an individual metabolic needs can change drastically, requiring dynamic changes in cells and tissues that regulate homeostasis. During pregnancy (Marynissen et al., *Diabetes* 36:883–891, 1987) β-cell mass increases, as well as in response to obesity (Kloppel et al., *Surv. Synth. Pathol. Res.* 4:110–125, 1985). These increases in β-cell mass are attributed to an increased requirement for insulin to maintain normal glucose levels (Parsons et al., *Endocrinology* 130:1459–1466, 1992). It has also been shown that β-cell mass normally decreases post-partum, primarily by apoptosis (Scaglia et al., *Endocrinology* 136:5461–5468, 1995).

It is generally believed that increases in β-cell mass occurs in three ways: 1) an increase in cell size and function; 2) increased proliferation of mature β-cells; and/or 3) increased,recruitment and differentiation of β-cell progenitors. In diabetic mice, animals that received islet transplants and then achieved normal glycemia, showed β-cell hypertrophy, rather than an increase in cell replication (Montana et al., *J. Clin. Invest.* 91:780–787, 1993). Adult β-cell regeneration has been demonstrated in rodents (Hellerstrom et al., in "The Pathology of the Endocrine Pancreas in Diabetes", P. J. Lefebvre and D. G. Pipeleers, eds., pp. 141–170, Springer-Verlag, Heidelberg, 1988). In partially pancreatectomized rats both preexisting β-cells, as well as proliferation and differentiation of precursor cells, have been demonstrated to expand (Bonner-Weir, *Diabetes Nutr. Res.* 5, *Supp.* 1:21–25, 1992).

Several factors have been shown to increase β-cell mass. These factors include glucose (Woerner, *Anal. Rev.* 71:33–57, 1938), IGF-I (Rabinovitch et al., *Diabetes* 31:160–164, 1982), reg protein (Terazono et al., *J. Biol. Chem.* 263:2111, 1988) and possibly a combination of TGF-α and gastrin (Bonner-Weir, *Recent Prog. Hormone Res.* 12:91–104, 1994). While some factors have been shown to increase β-cell mass in vitro or in vivo, understanding of the process is poorly understood and the possibility that other unidentified factors are involved is likely.

Recently a new member of the insulin superfamily has been identified, early placenta insulin-like factor or placentin (Chassin et al., *Genomics* 29:465–470, 1995). Placentin cDNA was isolated from first trimester human placenta and found to have a 139-amino acid open reading frame. Based on homology to the rest of the insulin superfamily it was predicted that placentin, like preprorelaxin and preproinsulin, would have a signal sequence, followed by the B chain, C peptide, A chain. The mature molecule would have the signal peptide and C peptide removed, with the B and A chains joined by both inter- and intra-chain disulfide bonds (Chassin et al., 1995, ibid. and James et al., *Nature* 267:544–546, 1977). The B-chain, C-peptide, A-chain motif is found in several other proteins, including relaxin (U.S. Pat. No. 4,835,251), insulin-like growth factors (IGF) I and II (Bang and Hall, in "Insulin-like Growth Factors", P. N. Schofield (ed.), pp. 151–177, Oxford University Press, Oxford, 1992), and Leydig Factor (Bullesbach et al., *J. Biol. Chem.* 270:16011–16015, 1995). Unlike other members of the insulin superfamily, IGF I and IGF II have D and E domains that are cleaved post-translationally. Cysteines that are involved in disulfide bonds are conserved in.all the members of the family and play a role in the tertiary structure of the molecules.

Placentin has been shown to stimulate $^3$H-thymidine uptake in human placental 3AsubE cells and stimulate human chorionic gonadotropin production in primary cultures of trophoblasts (Koman et al., *J. Biol. Chem.* 271:20238–20241, 1996). This activity suggests that placentin may play a role during placental development. However, the present inventors, surprisingly, have found that a molecule encoded by the DNA for placentin, but a different amino acid structure, increases β-cell mass and may be useful in treatment of diabetes, and further that the biologically active molecule differs from the molecule described in the art.

SUMMARY OF THE INVENTION

The present invention provides proteins produced by a method comprising: culturing a host cells into which has been introduced a DNA expression vector comprising a transcription promoter; a DNA segment comprising a nucleotide sequence as shown in SEQ ID NO: 1 from nucleotide 76 to nucleotide 417; and a transcription terminator, wherein said host cell expresses the polypeptide encoded by said DNA segment and recovering said protein.

In another embodiment, the host is a mammalian cell. In another embodiment, the host has had a second DNA expression vector introduced into it, wherein the second expression vector comprises a transcription promoter; a DNA segment encoding an endoprotease; and a transcription terminator, wherein said host cell expresses the a DNA segment comprising a nucleotide sequence as shown in SEQ ID NO: 1 from nucleotide 76 to nucleotide 417 and said DNA segment encoded by the endoprotease.

In another aspect, the present invention provides an isolated and purified protein comprising a first polypeptide comprising an amino acid sequence as shown in SEQ ID NO: 2 from residue 26 (Ala) to residue 110 (Ser) or 114 (Arg); and a second polypeptide comprising an amino acid sequence as shown in SEQ ID NO: 2 from residue 115 (Ser) to residue 139 (Thr), wherein said first polypeptide and said second polypeptide are capable of disulfide associating.

In another aspect, the present invention provides an isolated and purified protein comprising a first polypeptide comprising an amino acid sequence as shown in SEQ ID NO: 2 from residue 26 (Ala) to residue 48 (Lys), 49 (Thr) or 50 (Phe); and a second polypeptide comprising an amino acid sequence as shown in SEQ ID NO: 2 from residue 115 (Ser) to residue 139 (Thr), wherein said first polypeptide and said second polypeptide are capable of disulfide associating.

In another aspect, the present invention provides a method of stimulating proliferation of pancreatic islet comprising administering to a mammal in need thereof, an amount of an isolated and purified polypeptide comprising: a first polypeptide comprising an amino acid sequence as shown in SEQ ID NO: 2 from residue 26 (Ala) to residue 110 (Ser) or 114 (Arg); and a second polypeptide comprising an amino acid sequence as shown in SEQ ID NO: 2 from amino acid residue 115 (Ser) to residue 139 (Thr), and wherein said first polypeptide and said second polypeptide are capable of disulfide associating, sufficient to produce a clinically significant increase in insulin secretory capacity.

In another aspect, the present invention provides a method of stimulating proliferation of pancreatic islets comprising administering to a mammal in need thereof, an amount of an isolated and purified polypeptide comprising: a first polypeptide comprising an amino acid sequence as shown in SEQ ID NO: 2 from residue 26 (Ala) to residue 48 (Lys), 49 (Thr) or 50 (Phe); and a second polypeptide comprising an amino acid sequence as shown in SEQ ID NO: 2 from amino acid residue 115 (Ser) to residue 139 (Thr), and wherein said first polypeptide and said second polypeptide are capable of disulfide associating, sufficient to produce a clinically significant increase in insulin secretory capacity.

In other embodiments, the present invention provide methods wherein the clinically significant increase in insulin secretory capacity results in a decrease in fasting plasma glucose levels.

In other embodiments, the present invention provide methods wherein the isolated and purified protein is administered in combination with an insulin sensitizer.

In another aspect, the present invention provides a method for stimulating in vitro proliferation of pancreatic islet cells comprising culturing islets with an amount of an isolated and purified protein comprising: a first polypeptide comprising an amino acid sequence as shown in SEQ ID NO: 2 from residue 26 (Ala) to residue 110 (Ser) or 114 (Arg); and a second polypeptide comprising an amino acid sequence as shown in SEQ ID NO: 2 from amino acid residue 115 (Ser) to residue 139 (Thr), and wherein said first polypeptide and said second polypeptide are capable of disulfide associating, sufficient to produce an increase in the number of islet cells as compared to islet cells cultured in the absence of the protein.

In another aspect, the present invention provides a method for stimulating in vitro proliferation of pancreatic islet cells comprising culturing islets with an amount of an. isolated and purified protein comprising: a first polypeptide comprising an amino acid sequence as shown in SEQ ID NO: 2 from residue 26 (Ala) to residue 26 (Ala) to residue 48 (Lys), 49 (Thr) or 50 (Phe); and a second polypeptide comprising an amino acid sequence as shown in SEQ ID NO: 2 from amino acid residue 115 (Ser) to residue 139 (Thr), and wherein said first polypeptide and said second polypeptide are capable of disulfide associating, sufficient to produce an increase in the snumber of islet cells as compared to islet cells cultured in the absence of the protein.

In other embodiments, the present invention provides methods wherein said cells are cultured in 0.1 ng/ml to 100 ng/ml of said protein.

DETAILED DESCRIPTION OF THE INVENTION

Figure 1:
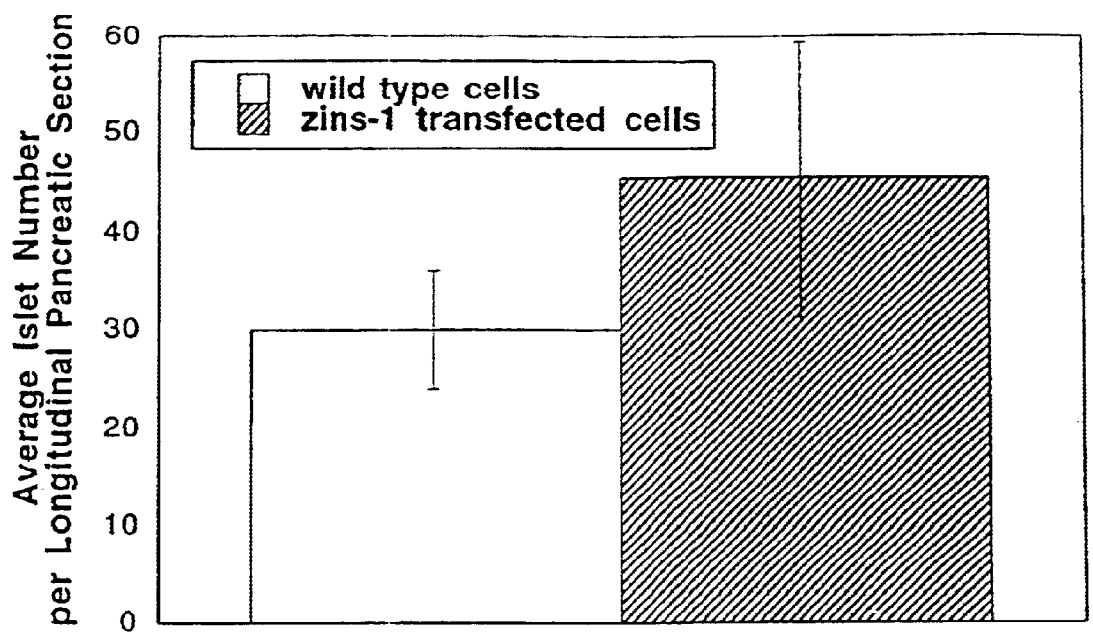
FIG. 1 illustrates that animals treated with BHK cells transfected with zins1 have a 50% increase in islet numbers over animals that have been treated with, untransfected BHK cells.

Prior to describing the present invention in detail, it may be helpful to define certain terms used herein:

The term "affinity tag" is used herein to denote a peptide segment that can be attached to a polypeptide to provide for purification of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–1210, 1988; available from Eastman Kodak Co., New Haven, Conn.), streptavidin binding peptide, or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "contig" denotes a polynucleotide segment equivalent in nucleotide sequence to an EST. A "contig assembly" denotes a collection of EST contigs that define a larger polynucleotide segment containing an open reading frame encoding a full-length or partial polypeptide.

The term "degenerate nucleotide sequence" denotes a sequence of nucleotides that includes one or more degenerate codons (as compared to a reference polynucleotide molecule that encodes a polypeptide) Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator The term "ortholog" (or "species homolog") denotes a polypeptide or protein obtained from one species that is the functional counterpart of a polypeptide or protein from a different species. Sequence differences among orthologs are the result of speciation.

The term "paralog" denotes a polypeptide or protein obtained from a given species that has homology to a distinct polypeptide or protein from that same species.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared, from a combination of natural and synthetic molecules.

A "polypeptide" is a polymer of amino acid residues joined by peptide bonds, whether produced naturally or synthetically. Small polypeptides are commonly referred to as "peptides".

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "promoter" denotes a portion of a gene containing DNA sequences that provide for the binding of RNA polymerase and initiation of transcription. Promoter sequences are commonly,. but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

All references cited herein are incorporated by reference in their entirety.

One aspect of the present invention is based in-part on the discovery that an insulin-homolog DNA previously described as placentin encodes a different polypeptide from that described as the placentin protein.

Another aspect of the present invention provides methods for administering the novel protein to stimulate pancreatic islet cells to proliferate in vivo and in vitro. Islet cell proliferation is a measure of increase in β-cell mass. Thus, the molecules of the present invention provide a means for increasing the size and number of β-cells (β-cell mass), and thereby increasing insulin availability.

The DNA sequence for placentin was reported to have a 139 amino acid codon open reading frame (WO 95/34653 and Chassin et al., 1995, ibid.), and was predicted to encode a secretory signal sequence and a mature polypeptide. The mature polypeptide was shown to have homology with insulin, relaxin 1 and 2, and Leydig Factor, and thus, was considered a member of the insulin superfamily. Within this family, the cysteine motif is highly conserved in the B and A chains, where the B chain motif can be represented as LCGX{10}C, where X{ } is the number of any amino acid residues except cysteine (as shown in SEQ ID NO: 6). The A chain motif is CCX{3}CX{8}C, where X{ } is the number of any amino acid residues, except cysteine (as shown in SEQ ID NO: 7).

Insulin is synthesized by β-cells of pancreatic islets as preproinsulin, and processing of the mature protein molecule involves cleavage at the C-terminus of the secretory signal polypeptide, and cleavage at the C-terminus of the B chain and at the N-terminus of the A chain, resulting in removal of the C-peptide. The cleavage sites for removal of the secretory signal peptide and C-peptide are not conserved within the insulin superfamily. Chassin et al. (*Genomics* 29:465–470, 1995) disclosed that the predicted mature placentin molecule would be cleaved at a serine (amino acid residue 17 of SEQ ID NO: 2) to remove the signal peptide and at leucine (amino acid residue 58 of SEQ ID NO: 2) and leucine (amino acid residue 109 SEQ ID NO: 2) to remove the C-peptide.

However, the present inventors predicted a different mature protein, which has been designated Zins1, comprising a disulfide-bonded B chain and A chain, wherein the B chain comprises the amino acid sequence of SEQ ID NO: 2 from amino acid residue 26 (Ala) to at least amino acid residue 43 (Cys) and wherein the A chain comprises the amino sequence of SEQ ID NO: 2 from amino acid residue 115 (Ser) to residue 139 (Thr), based on sequence alignment and analyses. Furthermore, the present inventors have isolated and purified the polypeptide from medium conditioned by host cells co-expressing a first DNA construct comprising the sequence of, SEQ ID NO: 1 from nucleotide 1 to nucleotide 420 with a second DNA construct encoding for endoprotease PC3. PC3 is one of several endoproteases shown to be restricted to endocrine and neuroendocrine tissues and is involved in prohormone processing. The Zins1 protein has demonstrated biological activity that resulted in increased β-cell mass and lowered blood glucose levels.

Analyses of the polypeptides present in the conditioned medium revealed polypeptides comprising a first polypeptide comprising amino acid residue 26 (Ala) to residue 110 (Ser) or 114 (Arg) as shown in SEQ ID NO: 2, and a second polypeptide comprising amino acid residue 115 (Ser) to residue 139 (Thr) as shown in SEQ ID NO: 2. These data suggest that the first polypeptide comprises a B chain and C-peptide and the second polypeptide comprises an A chain, wherein the first and second polypeptides are capable of disulfide associating.

Processing of the mature protein molecule involves cleavage at the C-terminus of the secretory signal peptide, and, based on predicted structural homology with other mature members of the insulin superfamily, a cleavage at the C-terminus of the B chain and at the N-terminus of the A chain, resulting in removal of the C-peptide. Alignment of the deduced amino acid sequence of the Zins1 polypeptide of the present invention with other known members of the insulin superfamily predicts a signal peptide cleavage site at amino acid residue 25 (Ala) of SEQ ID NO:2. Cleavage at the N-terminus of the A chain is predicted to be after amino acid residue 114 (Arg). The cleavage site at the junction of the C-peptide and A chain is highly conserved, occurring after Arg-X-X-Arg (wherein X is any amino acid residue), Arg-Arg or Lys-Arg; however, the cleavage sites at the junction of the signal sequence and B chain, and at the junction of the B chain and C-peptide, do not maintain a similarly high degree of conservation within the insulin family.

The C-peptide portion of insulin superfamily members is highly divergent. Also, the gene encoding Zins1 includes a silent intron of about 2 kb that interrupts the coding sequence in the C-peptide domain, adding another potential variable to the C-peptide portion of Zins1. Zins1 has a 139 amino acid open reading frame, compared to a 110 amino acid open reading frame for human insulin and about 100–200 amino acid open reading frames for other insulin superfamily members. Except for the IGFs (which contain D and E domains), the open reading frame length variations among the members of the insulin superfamily are predominantly associated with C-peptide variations in length.

The enzymology of proinsulin conversion suggests that prohormone convertase 3 (PC3) cleaves primarily at the B chain-C-peptide junction, and that PC2 cleaves preferentially at the C-peptide-A-chain junction and favors proinsulin already processed by PC3 over intact prohormone. In human and rat proinsulin, dibasic residues link the B chain and C-peptide and the C-peptide and A chain. In addition, a basic residue 4 residues N-terminal to the cleavage site (a "P4 basic residue") may be present at one or both junctions, and may influence the ability of PC3, PC2 or furin to cleave at the junction sites. In a study reported by F. Vollenweider et al. (*Diabetes* 44:1075–80, 1995), cotransfection of COS cells with PC3 and either human proinsulin, rat proinsulin II or mutant human proinsulin Arg$^{62}$ showed that PC3 cleaved both proinsulin junctions, regardless of the presence or absence of a P4 basic residue.

Zins1 does not have basic or dibasic residues from position 49 (Thr) to 62 (Gly), as shown in SEQ ID NO: 2. There is an Arg residue at position 63, and a Lys residue at positions 65, 74, 94, 95, 105 and 106. An Arg-Lys-Lys-Arg motif is also present at residues 111–114, just before the A chain start sequence described by the resent invention. Based on sequence alignments, nowledge of prohormone conversion enzymes, and the data resented herein, a B chain-C-peptide junction cannot be definitively determined. Chassin et al. (ibid.) describe a putative cleavage site at the junction of the B chain and C-peptide of placentin (INSL4) between residue 58 (Leu) and residue 59 (Leu) of SEQ ID NO:2. Koman et al. (ibid.) describe a putative cleavage site at the junction of the B chain and C-peptide of placentin between residue 62 (Gly) and residue 63 (Arg) of SEQ ID NO:2. However, neither group provides rationale or data to support cleavage at these sites.

Upon expression of the Zins1 molecule in mammalian cells, the present inventors have discovered that the C-peptide is glycosylated. Carbohydrate analysis revealed that 1 O-glycosylation site is present at either residue 49 (Thr), 50 (Thr), 51 (Thr) or 61 (Ser) of SEQ ID NO: 2. Based on homology with other members of the insulin superfamily, where O-glycosylation has not been identified in any B-chain, the B chain/C-peptide cleavage is predicted to occur after residue 48 (Lys) or residue 49 (Thr) or residue 50 (Phe) of SEQ ID NO: 2, with the O-glycosylation occurring at one of residues 51, 52, 53 or 61. Two more O-glycosylation sites are predicted at residues 69 (Ser), 70 (Thr), and/or 71 (Ser) of SEQ ID NO: 2. Another glycosylation site is predicted at either residue 81 (Thr), 82 (Thr), 83 (Ser) or 90 (Ser) of SEQ ID NO: 2.

While not wanting to be bound by theory, the B chain/C-peptide form of the Zins1 molecule may have an important role in the biological function of the molecule. The B chain/C-peptide may form a domain that is involved in directing the molecule to its target; processing of the molecule to its biologically active form; regulation of receptor multimerization and involvment in formation of tertiary structure, such as folding. In addition, the C-peptide, particularly in light of the putative glycosylation sites, may function as an independent molecule.

Therefore, the present invention provides isolated Zins1 proteins that are substantially homologous to the polypepitides of SEQ ID NO: 2. In one embodiment, the isolated and purified Zins1 proteins comprise a first polypeptide (B chain) comprising the amino acid sequence of SEQ ID NO: 2 from amino acid residue 26 (Ala) to at least amino acid residue 43 (Cys) and a second polypeptide (A chain) comprising the amino sequence of SEQ ID NO: 2 from amino acid residue 115 (Ser) to residue 139 (Thr), wherein said first and second polypeptides are capable of disulfide associating; and their allelic variants and orthologs.

In another embodiment, the present invention provides isolated and purified Zins1 proteins that comprise a first polypeptide comprising the amino acid sequence of SEQ ID NO: 2 from amino acid residue 26 (Ala) to an amino acid residue selected from the group consisting of 48 (Lys), 49 (Thr) and 50 (Phe); and a second polypeptide comprising the amino sequence of SEQ ID NO: 2 from amino acid residue 115 (Ser) to residue 139 (Thr), wherein said first and second polypeptides are capable of disulfide associating; and their allelic variants and orthologs.

In another embodiment, the present invention provides isolated and purified Zins1 protein that comprise a first polypeptide comprising the amino acid sequence of SEQ ID NO: 2 from amino acid residue 26 (Ala) to amino acid residue 110 (Ser) or 114 (Arg) and a second polypeptide comprising the amino sequence of SEQ ID NO: 2 from amino acid residue 115 (Ser) to residue 139 (Thr), wherein said first and second polypeptides are capable of disulfide associating; and their allelic variants and orthologs. Cleavage at the C-peptide/A chain junction occurs at residue 114 (Arg), but carboxypeptidases are well known to remove dibasic residues resulting in the final C-peptide C-terminus being between residue 114 (Arg) and residue 110 (Ser).

The term "substantially homologous" is used herein to denote polypeptides having 50%, preferably at least 80%, more preferably 90% identical and most preferably 95% or more identity to the polypeptides as shown in SEQ ID NO: 2.

Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes).

The percent identity is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occuring amino acid residues. Non-naturally occuring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occuring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996) Within a third method, *E. coli* cells are cultured in the absence of a natural amino acid that is to be replaced (e.g., phenylalanine). and in the presence of the desired non-naturally occuring amino acid(s) (eg., 2-azaphenylalanine, 3-azaphenylalanine, 4-azaphenylalanine, or 4-fluorophenylalanine). The non-naturally occuring amino acid is incorporated into the protein in place of its natural counterpart. See, Koide et al., *Biochem.* 33:7470–7476, 1994. Naturally occuring amino acid residues can be converted to non-naturally occuring species by in vitro chemical modification. Chemical modification can be combined with site-directed mutagenesis to further expand the range of substitutions (Wynn and Richards, *Protein Sci.* 2:395–403, 1993).

Essential amino acids in the polypeptides of the present invention can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity (e.g., proliferation of islet or β-cells) to identify amino acid residues that are critical to the activity of the molecule.

Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of mature, biologically active polypeptides that are derived from polynucleotides that are substantially homologous to nucleotides 76 to 417 of SEQ ID NO: 1 or allelic variants thereof and retain the properties of the wild-type protein to stimulate islet proliferation, differentiation and/or metabolic processes.

Suitable host cells are those cell types that can be transformed or transfected with exogenous DNA and grown in culture, and include bacteria, fungal cells, and cultured higher eukaryotic cells. Eukaryotic cells, particularly culture cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a Zins1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zins1 polypeptide into the secretory pathway of a host cell, a secretory signal sequence (also known as a leader sequence, prepro sequence or pre sequence) is provided in the expression vector. The secretory signal sequence may be that of the Zins1 polypeptide, or may be derived from another secreted protein (e.g., t-PA) or synthesized de novo. The secretory signal sequence is joined to the Zins1 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

If Zins1 polypeptide is expressed in a non-endocrine or non-neuroendocrine cell, the expression host cell generally will not express the prohormone convertases PC2 and PC3, which are believed to be involved in the regulated secretory pathway. Another member of this endoprotease family, furin, is present in most cells and is believed to be involved in the constitutive secretory pathway. F. Vollenweider et al. have described the role of these prohormone conversion endoproteases in general, and specifically describe studies involving co-transfection of COS cells with proinsulin and one of the endoproteases (*Diabetes* 44:1075–80, 1995). Their results showed that PC3 and furin were able to cleave proinsulin at both its junctions; PC2 did not exhibit prohormone cleavage to any significant extent. Without co-transfection of an endoprotease, the prohormone was not converted to any great extent by COS cells. However, the co-transfection system described is still not an exact model of the natural β cell environment, since β cells make both PC2 and PC3. Also, a non-endocrine cell does not represent a native environment for PC2 and PC3 expression. In addition, co-transfection may result in general or local overexpression of PC2 and/or PC3, relative to the native β cell environment. In a preferred embodiment, the host cells will be co-transfected with a second DNA expression construct comprising the following operably linked elements: a transcription promoter; a DNA segment encoding an endoprotease; and a transcription terminator, wherein the host cell expresses the DNA segment encoding the endoprotease.

Cultured mammalian cells are preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (*Bangalore*) 1:47–58, 1987.

Fungal cells, including yeast cells, and particularly cells of the genus Saccharomyces, can also be used within the present invention, such as for producing Zins1 fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Zins1 polypeptides can also be used to prepare antibodies that specifically bind to Zins1 epitopes, peptides or polypeptides. Methods for preparing polyclonal and monoclonal antibodies are well known in the art (see, for example, Sambrook et al., *Molecular Cloning: A Laboratory Manual, Second Edition*, Cold Spring Harbor, N.Y. 1989; and Hurrell, J. G. R., Ed., *Monoclonal Hybridoma Antibodies: Techniques and Applications*, CRC Press, Inc., Boca Raton, Fla., 1982, which are incorporated herein by reference). As would be evident to one of ordinary skill in the art, polyclonal antibodies can be generated from a variety of warm-blooded animals, such as humans, horses, cows, goats, sheep, dogs, chickens, rabbits, mice and rats.

The immunogenicity of a Zins1 polypeptide may be increased through the use of an adjuvant, such as alum (aluminum hydroxide) or Freund's complete or incomplete adjuvant. Polypeptides useful for immunization also include fusion polypeptides, such as fusions of Zins1 polypeptides or a portion thereof with an immunoglobulin polypeptide or with a maltose binding protein. The polypeptide immunogen may be a full-length molecule or a portion thereof. If the polypeptide portion is "hapten-like", such a portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to Zins1 polypeptides or peptides, and selection of antibody display libraries in phage or similar vectors (for instance, through use of immobilized or labeled Zins1 polypeptide or peptide).

Antibodies are defined to be specifically binding if they bind to a Zins1 polypeptide with a binding affinity ($K_a$) of $10^6$ $M^{-1}$ or greater, preferably $10^7$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to Zins1 polypeptides or peptides. Exemplary assays are described in detail in *Antibodies: A Laboratory Manual*, Harlow and Lane (Eds.), Cold Spring Harbor Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant Zins1 polypeptides or peptides.

Antibodies to Zins1 polypeptides may be used for tagging cells that express Zins1 polypeptides; for isolating Zins1 polypeptides by affinity purification; for diagnostic assays for determining circulating levels of Zins1 polypeptides; for detecting or quantitating soluble Zins1 polypeptides as marker of underlying pathology or disease; in analytical methods employing FACS; for screening expression libraries; for generating anti-idiotypic antibodies; for localization by immunocytochemistry; and as neutralizing antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anticomplement pairs as intermediates. Antibodies herein may also be directly or indirectly conjugated to drugs, toxins, radionuclides and the like, and these conjugates used for in vivo diagnostic or therapeutic applications.

Zins1 polypeptide prepared according to the present invention is purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography, Q-Fast Flow Sepharose, MonoQ resin, FPLC, phenyl Sepharose, hydroxyapatite, Mono S and/or S-Sepharose.

Molecules of the present invention can be used to identify and isolate receptors for Zins1. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993. and Fedan et al., *Biochem. Pharmacol.* 33:1167–1180, 1984) and specific cell-surface proteins can be identified.

Antibodies to Zins1 proteins and peptides may be used for affinity purification, for diagnostic assays, for determining circulating levels of Zins1 polypeptides and as antagonists to block Zins1 binding and signal transduction in vivo and in vitro.

Proteins of the present invention are useful for stimulating proliferation or differentiation of pancreatic islets and their component cells which include α-cell, β-cells and δ-cells. Proliferation and differentiation can be measured in vitro using cultured cells or in vivo by administering molecules of the claimed invention to the appropriate animal model. For instance, Zins1 transfected or Zins1-endoprotease co-transfected expression host cells may be embedded in an alginate environment and. injected (implanted) into recipient animals. Alginate-poly-L-lysine microencapsulation, permselective, membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments. can extend the life of the injected cells from a few hours or days (naked cells) to several weeks (embedded cells). The alginate threads, described herein provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulatable and the methodology is scalable for preparation of numerous threads.

Molecules of the present invention are useful as a reagent for in vitro culturing of islets, and hence their component cells which include α-cell, β-cells and δ-cells, in vitro, which have been difficult to grow. Cultured islets provide islet cells for transplantation, an alternative to whole pancreas transplantation. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

Zins1 may also have other insulin-like activities, affecting glucose and lipid metabolism. Assays to measure other cellular responses, that include chemotaxis, adhesion, changes in ion channel influx, regulation of second messenger levels and neurotransmitter release are well known in the art. See, for example, in "Basic & Clinical Endocrinology Ser., Vol. Vol. 3," *Cytochemical Bioassays: Techniques & Applications*, Chayen; Chayen, Bitensky, eds., Dekker, N.Y., 1983.

Treatment of diabetes using Zins1 will be particularly useful for gestational and Type II (NIDDM) diabetes. In gestational and Type II diabetes, the disease is characterized by defects in both insulin action (also referred to as insulin resistance) and insulin secretion. In some patients, the use of Zins1 alone may be sufficient to eliminate the requirement for exogenous insulin or insulin secretagogues (oral hypoglycemic agents). Zins1 may be used in conjunction with insulin, with insulin sensitizing agents, and oral hypoglycemic agents or with combinations thereof. Troglitazone is an example of an insulin sensitizing agent. In an exemplary Zins1-insulin sensitizer combined treatment, the recipient's insulin resistance is reduced, thereby decreasing the insulin secretion demand, and insulin secretion capacity is enhanced by increases in β-cell mass. Such a treatment provides a β-cell reserve and results in effective treatment for gestational and Type II diabetes. Zins1 may provide treatment for Type I diabetes, if treatment includes suppression of autoantigenic destruction of β-cells once they are stimulated to proliferate and increase in function.

For pharmaceutical use, the proteins of the present invention are formulated for parenteral, particularly intravenous or subcutaneous, delivery according to conventional methods. Insulin formulations are known in the art and can provide guidance for molecules of the present invention. Intravenous administration will be by bolus injection or infusion over a typical period of one to several hours. In general, pharmaceutical formulations will include a mature Zins1 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishihg Co., Easton Pa., 1990, which is incorporated herein by reference. Therapeutic doses will generally be in the range of 0.1 to 100 μg/kg of patient weight per day, preferably 0.5–20 μg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days. In the treatment of diabetes, the molecules of the present invention would be used in chronic treatment, over several months or years. In gestational diabetes, chronic administration would generally be for weeks. In general, a therapeutically effective amount of Zins1 is an amount sufficient to produce a clinically significant change in insulin secretory capacity. In a patient, insulin secretory capacity is determined by fasting plasma glucose levels or glucose tolerance. Generally, fasting plasma glucose levels equal to, or more than, 126 mg/dl indicate diabetes. Impaired glucose tolerance is diagnosed when 2-hour plasma glucose levels from a oral glucose tolerance tests are greater than, or equal to, 140 mg/dl, but less than 200 mg/dl. Above 200 mg/dl, diabetes is diagnosed. Generally, treatment would begin when fasting plasma glucose levels are above 126 mg/dl. Normal plasma glucose levels are 115 mg/dl, according to standards set by the American Diabetes Association.

The invention is further illustrated by the following non-limiting examples.

EXAMPLES

Example 1

Expression of a Biolocically Active Zins1

The Zins1 cDNA was isolated from a human placental library using PCR and designated Zins1. The Zins1 cDNA sequence was prepared in a mammalian expression vector with either a N-terminal or C-terminal poly-His tag. The mammalian expression vector was modified from a vector designated pHZ-200. pHZ-200 was derived from a mammalian expression vector designated pHZ-1 with the only modification being that the dihydrofolate reductase sequence was substituted for the neomycin resistance gene. Plasmid pHZ-1 is an expression vector used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning. banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator.

The vector used for the N-terminal His tagged Zins1, was designated pOZ2, and contained at the 5' end of the cloning site, a tPA leader followed by six histidine residues and a four amino acid spacer (GGSG), as shown in SEQ ID NO: 4 from amino acid residue 36 to residue 45. The final Ser, Gly residues of the spacer constitute a BspE1 restriction site, allowing for insertion of the desired cDNA with no extra residues. The downstream 3' cloning site was Xho1. The zins1 sequence was inserted into the BspE1/Xho1 site directionally with the predicted mature end of the protein at the 5' end amino acid residue 26 (Ala) of SEQ ID NO: 2. The Xho site occurs directly after an in-frame stop codon. This construct was designated Zins1pOZ2.

The C-terminal His tagged Zins1 construct was made in pOZ1. This vector is pHZ-200 based with a Kpn1 site at the 5' end of the cloning site. At the 3' end the vector contains an in-frame spacer (GSGG) followed by six histidine residues. The first two residues of the spacer (GS) constitute a BamHI site which allows for insertion of the cDNA of interest with no extra residues. The zins1 sequence, containing the native leader sequence, was inserted directionally using the Kpn1/BamHI site. A stop codon occurs after the final His residue. This construct was designated Zins1pOZ1.

The zins1 cDNAs were each co-transfected into BHK 570 cells (ATCC accession no. 10314) along with cDNA encoding one of two different conversion endoproteases known to be involved in prohormone processing. These two enzymes, PC2 and PC3, have been shown to be restricted to endocrine and neuroendocrine tissues and cells, with PC3 resulting in more extensive processing of insulin from its prohormone to active form.

A total of four transfections were performed:
1) zins1pOZ1/PC2 (called zins1C/PC2)
2) zins1pOZ1/PC3 (called zins1C/PC3)
3) zins1pOZ2/PC2 (called zins1N/PC2) and
4) zins1pOZ2/PC3 (called zins1N/PC3).

10 µg of each DNA prep (20 µg total) was ransfected into subconfluent BHK570 cells using ipofectamine reagent (GIBCO-BRL, Gaithersburg, Md.), ccording to the manufacturer's specifications. The following day the transfected cells were trypsinized, and split at several dilutions up to 1:160. The medium was replaced with growth media (Table 3) containing both 1 µM methotrexate (MTX) and 1+ G418 (neomycin). The pOZ plasmids contain the DHFR gene conferring resistance to MTX and the plasmid containing the PC enzyme contains the neomycin resistance gene. After several weeks, transfectant pools that had been cultured in 1 µM MTX+G418, and approximately 12 individual clones from each transfection were selected for further analyses.

Serum-free conditioned media (Table 4) from each of the pools and clones were analyzed for reactivity with an antibody made to a zins1/MBP fusion protein. The recombinant zinsi protein was affinity purified from the spent culture media using Ni-NTA agarose (Qiagen, Chatsworth, Calif.). Purification was done using a batch process, where 200 µl of Ni resin was added to 5 ml of conditioned media and incubated overnight on a rocking platform at 4° C. The resin was washed 2 times and the proteins eluted directly into 2× tricine gel sample buffer. The samples were electrophoresed on 16% Novex tricine gels and blotted onto nitrocellulose. The blots were incubated overnight in a 1:2000 (0.5 µg/ml) dilution of the fusion protein antibody.

The blots revealed a broad band of immunoreactivity between 10–18 kDa under reducing conditions, with distinct bands at 3 and 6 kDa in some lanes. Several clones were picked for further analysis; zins1N/PC3#4, zins1N/PC3#3, zins1N/PC3#9, zins1N/PC2#1, zins1C/PC2#2, zins1C/PC3#9, and zins1C/PC3#1.

N-terminal amino acid sequencing was performed on several clones. Two bands were sequenced from zins1N/PC2 #1. The lower band (~3 kDa) was found to have the sequence SGRHRFDPFXXEVIXDDGTSVKL (amino acid residues 115 to 123 of SEQ ID NO: 2, wherein X is Cys), representing the A chain of the molecule. A band slightly above this (~6 kDa) was sequenced and found to be SQEIHAEFQR-GRRHHHHHGGSGAELRGXG (amino acid residues 23 to 52 of SEQ ID NO: 4, wherein X is Cys). The first 13 residues are part of the tPA leader that was not removed in processing.

Several bands were also sequenced from zins1C/PC3#9 (this molecule contained the native leader and a C-terminal His tag). Bands of 14.5, 9.0, 8.0 and 3.5 kDa were sequenced. The first three bands all started with AELRGCG (amino acid residues 26 to 32 of SEQ ID NO: 2), which appeared to be the N-terminus of the mature zins1 protein (B-chain). The 3.5 kDa band started with SGRHRFD (amino acid residues 115 to 121 of SEQ ID NO: 2), representing the N-terminus of the A-chain.

It was believed that a tag on the N-terminus of the B-chain was less likely to interfere with bioactivity than one on the C-terminus of the A-chain. Two clones with relatively high expression of processed protein were chosen for use in the alginate threads assay (see Example 2). These two cell lines, zins1N/PC3#3 and zins1N/PC2#1, differ only by the enzyme co-transfected for prohormone processing. The A-chain produced by these two lines was identical. The B-chain of zins1N/PC2#1 was sequence analyzed and contained some of the tPA leader. Zins1N/PC3#3 demonstrated biological activity in the alginate threads assay (as described in Example 2), and zins1N/PC2#1 did not, suggesting that zins1N/PC3#3 was properly processed in this in vivo assay.

TABLE 3

Growth Medium 500 ml Delbecco's Modified Eagle's Medium (DMEM) (Gibco BRL)
5% fetal calf serum (Hyclone, Logan, UT)
(1 mM) sodium pyruvate (Irvine, Santa Ana, CA)
(.29 mg/ml) L-glutamine (Hazelton, Lenexa, KS)
1x PSN (5 mg/ml penicillin, 5 mg/ml streptomycin, 10 mg/ml neomycin) (Gibco BRL, Gaithersburg, MD)

TABLE 4

Serum-free Medium 500 ml Dulbecco's Modified Eagle's Medium (DMEM; Gibco BRL)
(1 mM) sodium pyruvate (Irvine, Santa Ana, CA)
(.29 mg/ml) L-glutamine (Hazelton, Lenexa, KS)
(1 mg/ml) vitamin K (Merck, Whitehouse Station, NJ)
(10 mg/ml) transferrin (JRH, Lenexa, KS)
(5 mg/ml) fetuin (Aldrich, Milwaukee, WI)
(2 ug/ml) selenium (Aldrich, Milwaukee, WI)

Example 2

In Vivo Testing of Zins1 (Zins1)

A. Xenogeneic Cell Transplantation of Zins1 Gene
i. Preparation of Zins1 Alginate Threads Briefly, 3% alginate was prepared in USP for injection sterile $H_2O$ (several hours on a rotary shaker at R.T., to get the alginate into solution), and sterile filtered using an 0.8 $\mu M$ filter flask (again, several hours to achieve filtration). Just prior to preparation of alginate threads, the alginate solution was again filtered through a 0.45 $\mu M$ syringe tip filter.

A suspension (containing about $10^6$ to about $10^8$ cells/ml) was mixed at 1:1 vol/vol with the 3% alginate solution. One ml of this alginate/cell suspension was extruded from a 1 cc syringe through a 30 g needle into a 100 mM $CaCl_2$ solution (sterile filtered through a 0.22 $\mu M$ filter), forming a "thread". The extruded thread was incubated for about 15 min in the 100 mM $CaCl_2$ solution; then transferred into a solution of 50 mM $CaCl_2$; and then into a solution of 25 mM $CaCl_2$. The thread was then rinsed with deionized water before incubation in Latctated Ringer's Solution until the time of injection. Finally, the thread in Lactated Ringer's Solution was drawn into a 3 cc syringe barrel (without needle attached). A large bore needle (16 g) was then attached to the syringe, and the thread was intraperitoneally injected into a recipient mouse in ~1.5 ml total volume of the Lactated Ringer's Solution.

In one study, each member of a group (containing six female, one year old BALB/c mice) was injected with a thread containing either $1×10^6$ wild type (untransfected) BHK cells; $2×10^6$ zins1N/PC3#3 co-transfected cells; or $4×10^6$ zins1N/PC2#1 co-transfected cells. Blood was drawn at days 12 and 15 (non-fasted), and at day 19 (fasted), and serum glucose levels (days 12, 15 and 19) and serum insulin levels (days 12 and 15) were determined, as well as cell counts, complete blood chemistries and complete blood counts (CBCs). The animals that received the zins1N/PC3#3 threads showed lower serum glucose levels at days 12 and 19 than the wt BHK and zins1N/PC2#1 threads-injected animals. At day 12, the zins1N/PC3#3 threads-injected animals showed elevated serum insulin levels, as compared to the other two groups. Among all of the groups of animals, CBCs were comparable.

In a second study, 7 and 6 female BALB/c mice (female, 9 weeks old) were intraperitoneally injected at day 0 with threads containing about $3×10^7$ untransfected BHK cells or threads containing about $5×10^6$ zins1N/PC3#3 co-transfected cells, respectively. Another control group of 3 animals received no treatment.

All of the animals were fasted prior to being bled on days −3, 8, 12 and 27. For fasting, food was removed at the end of the previous day's light cycle. The animals experienced a dark cycle without food, and then the animals were bled after the beginning of the next light cycle. Thereafter, food was restored. At days 8 and 12, the animals that were injected with zins1N/PC3#3 threads exhibited a significant decrease in serum glucose (35 and 48 mg/dl, respectively), as compared to animals that were injected with wild type BHK cells (65 and 90 mg/dl, respectively). Serum glucose was determined using serum obtained from whole blood collected in non-heparinized tubes. The blood was centrifuged immediately and the serum was analyzed for glucose concentration. Serum triglyceride levels were also significantly higher at days 8 and 12 in the animals that were injected with zins1N/PC3#3 threads (91 and 60 mg/dl, respectively), as compared to animals that were injected with wild type BHK cells (42 and 23 mg/dl, respectively). The zins1N/PC3#3 threads-injected animals exhibited body weights and serum cholesterol levels comparable to those of the wild type BHK threads-injected animals, and did not appear or behave differently from the wild type BHK threads-injected animals.

In a third study, 8 month old db/db mice (very obese, severely diabetic) were injected with wild type BHK threads containing $4×10^7$ cells (n=7) or with zins1N/PC3#3 threads containing $4×10^7$ cells (n=6). Non-fasted animals were bled on days −4, 7, 13 and 17. At day 13, blood urea nitrogen levels (an indicator of kidney function) were lower in the animals that received zins1N/PC3#3 threads, as compared to the BHK threads control group.

ii. Histology and Histomorphometry

The pancreas and spleen, a portion of the small intestine, omentum and any omental fat that might include pancreas were collected from 15 mice.

The tissues were fixed in 10% NBF (neutral buffered formalin; Surgipath, Richmond, Ill.) overnight. The pancreatic lobes were pressed together slightly to expose the largest pancreatic area to make every lobe of the pancreas flatten.

The tissue was dehydrated with a graded series of ethyl alcohols, cleared with xylenc, and infiltrated with PARA-PLAST X-TRA (Fisher Scientific, Pittsburgh, Pa.) using a TISSUE-TEK VIP2000 (Miles, Inc., Elkhart, Ill.).

The flattened pancreas was removed from the biopsy bag using forceps and embedded longitudinally with PARA-PLAST X-TRA. All pancreata were oriented the same way in the block, with the head of the pancreas placed in one corner of the embedding mold, the tail of the pancreas in the opposite corner, and the body in the middle of the mold.

Each section was trimmed with a Jung Biocut 2035 microtome (Bartels and Stout, Inc., Bellevue, Wash.) until the largest pancreatic profile area was exposed. Sections were cut at 3 $\mu m$ in thickness.

The sections were stained with Harris hematoxylin (Sigma, St. Louis, Mo.) and Eosin histology staining (Surgipath, Richmond, Ill.). The number and size of islets per longitudinal section of the pancreas were counted and measured by using a camara-lucida attached to a light microscope (10× objective, Olympus, BH-2), interfaced to a BIOQUANT SYSTEM IV image analysis system (B&M Biometric, Inc., Nashville, Tenn.). After calibration, the electronic pen of the digitizer was used to carefully trace the outline of each islet profile by screening the whole section of the pancreas. Simultaneously, the data was computed and stored. Data analyses were performed by using ANOVA (GraphPad Software, San Diego, Calif.) followed by unpaired t test.

Figure 2:
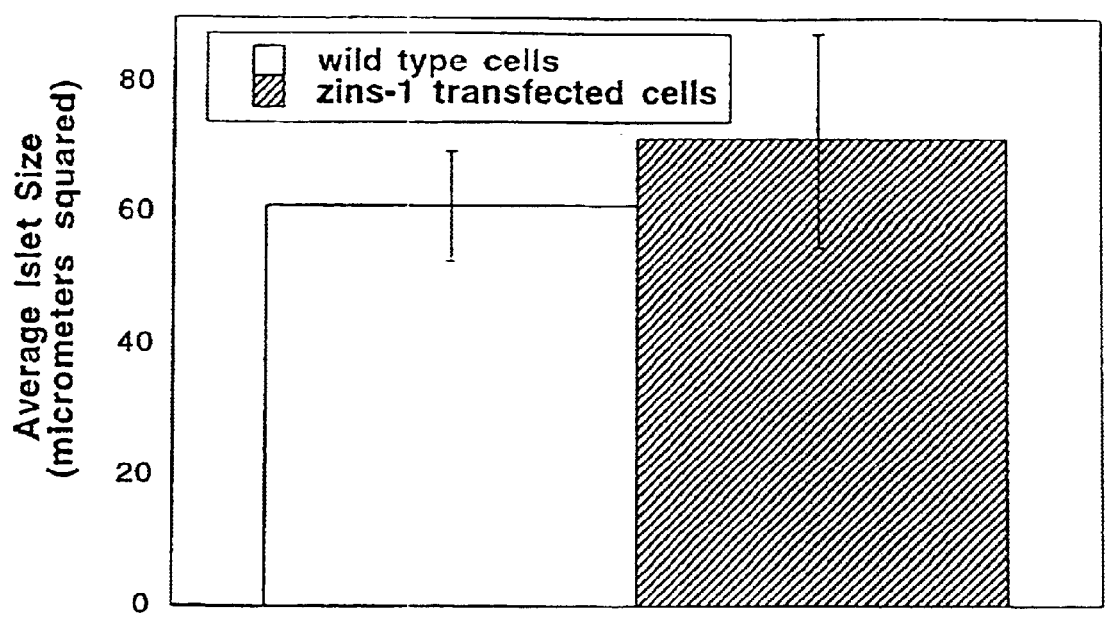
FIG. 2 illustrates that animals treated with BHK cells transfected with, zins1 have a trend toward increased islet size over animals treated with untransfected BHK cells.

The results are shown in FIG. 1 and FIG. 2. FIG. 1 illustrates a 50% increase in the number of islets present in samples taken from animals treated with BHK cells transfected with zins1 over animals treated with untransfected BHK cells. FIG. 2 illustrates a trend toward increased size of islets seen in animals treated with BHK cells transfected with zins1 versus animals treated with untransfected BHK cells.

B. Administration of Zins1 Purified Protein

Purified, zins1, that is produced by co-expressing the protein with PC3, is administered to normal mice to evaluate the effects on blood glucose and pancreatic islet histomorphometry. The duration of the study is 27 days with dosing for 20 days.

Female Balb/c mice, approximately nine weeks old are divided into the following treatment groups.

Group 1: Vehicle (0.1% BSA/PBS), ip, n=10
Group 2: 1 μg zins1/PC3 per mouse (50 μg/kg), ip, n=10
Group 3: 5 μg zins1/PC3 per mouse (250 μg/kg), ip, n=10
Group 4: Untreated, n=10

On day 0, mice are weighed, ear tagged and injected with 0.1 ml of the appropriate treatment solution. Animals are checked daily for behavioral and grooming changes, and body weights are determined weekly.

Labeling with BrdU (Zymed Laboratories, South San Francisco, Calif.), according the manufacturer's specifications is done from days 8–11 and from days 17–19 to label islet cells that are dividing in response to zins1.

Animals are bled on day 8 (a non-fasting sample) under ether anesthesia for clinical chemistry.

Mice are weighed and bled for serum on day 28. At necropsy, on day 28, the pancreas and a piece of gut for BrdU control are collected. The pancreas is processed for histomorphbmetric analysis of islet size and number as described in A.ii., above. In addition, total cells and islets are analyzed for BrdU incorporation as described in Ellwart et al., *Cytometry* 6:513–520, 1985.

Example 3

Purification and Characterization of Zins1 Protein

A. Purification of Zins1 Protein

The construct encoding the 124 amino acid Zins1 NF+PC3 (Zins1poZ2/PC3; described in Ex. 1) expressed in BHK cells was purified by affinity chromatography on anti-flag Sepharose (Eastman Kodak, Rochester, N.Y.), according to the manufacturer's specifications. Antigen was eluted with flag peptide, and further purified by gel filtration chromatography on Sepharose G-50 (Eastman Kodak). A total of 4.5 mg of Zins1 NF+PC3 was purified.

Analysis of the purified material by nonreducing SDS-PAGE, followed by staining with Coomassie Blue, revealed a mixture of at least four peptides of apparent molecular weights 14,000–25,000. By staining, each of the four peptides was present in approximately equimolar amounts and each of these bands appeared to cross react with anti-Flag antibodies upon Western blotting. Under reducing conditions, the electrophoretic profile was altered with each of bands exhibiting somewhat greater electrophorectic mobility. In addition, the major Coomassie Blue-stained protein observed under these conditions was a protein of ~4 kDa. This band did not cross react with anti-Flag antibodies on Western blots.

Purified Zins 1NF+PC3 was probed on Western blots with each of three anti-Zins 1 peptide antibodies and anti-Flag antibodies as a control. The peptides used for antibody production in rabbits were:

Zins1-DC-1, LSQLLRESLAAELRG, residues 16 to 30 of SEQ ID NO: 2 (spanning the putative N-terminus/"B" chain junction);

Zins1-DC-2, LLESGRPKEMVSTSNNKD, residues 57 to 75 of SEQ ID NO: 2 (the amino terminus of the "B" chain/"C" chain junction as predicted by Chassin et al., 1995, ibid.);

Zins1-DC-3, LKKIILSRKKRSGRHR, residues 104 to 119 of SEQ ID NO: 2 (spanning the putative "C" chain/"A" chain junction)

The anti-Zins 1-DC-1 antibody did not react with any band on reducing or nonreducing SDS-PAGE gels. Since only the five C-terminal residues of this peptide (i.e., residues 26–30 of SEQ ID NO: 2) were contained within the sequence of Zins1pOZ2/PC3, this indicated that no antibodies to this sequence were present. The lack of immunoreactivity also suggested that Zins1pOZ2/PC3 is correctly flag-tagged, since no crossreactivity was observed to amino acids N-terminal to the "B" chain junction.

The anti-Zins1 DC-3 did not react with any peptides on the Western blots, as well. These antibodies were directed against a peptide that spans the putative "C" chain/"A" chain junction. These results suggested that this region was cleaved during processing of the Zins1, a finding consistent with the PVDF blotting/sequencing. Lack of immunoreactivity with larger or smaller bands (unprocessed "B/C+A" or processed "B/C" and "A" chain) suggested that the epitope was at the "C" chain/"A" chain junction.

Results obtained with the anti-Zins1-DC-2, antibodies directed against a peptide from the putative "C"-peptide, were different. The reactivity looked identical to that observed with anti-Flag antibodies, namely reactivity was seen in several bands around ~20 kDa. These bands showed a small decrease in apparent size upon reduction.

B. Characterization of Zins1 Protein

The N-terminally tagged Zins1 protein purified above was characterized using N-terminal sequence analysis, glycosidase PAGE analysis, monosaccharide composition analysis and mass spectral analysis.

N-terminal sequence analysis was done as follows:

A sample of Zins 1, purified as described above, was run on a NOVEX 18% Tris-Glycine gel (NOVEX, San Diego, Calif.) under reducing conditions (2-mercaptoethanol). An electroblot transfer to PVDF membrane was performed in 10 mM CAPS buffer pH 11.0, 10% methanol at 200 mA for 1 hour at 4° C. The PVDF blot was visualized with Coomassie blue staining. Stained protein bands were excised for Edman degradation N-terminal protein sequencing on an Applied Biosystems 476A Protein Sequencer (Foster City, Calif.) using standard protocols and FSTBLT cycles. The data was analyzed using Applied Biosystems Model 610A Data Analysis System, v. 1.2.2).

Liquid Chromatography—Mass Spectrometry (LCMS) was performed as follows:

A Michrom BioResources MAGIC 2002 HPLC system (Michrom BioResources, Inc., Auburn, Calif.) equipped with a 1.0×150 mm Monitor C18 100 Å 5 m column (Michrom BioResources, Inc.) was used at a flowrate of 50 μl/min and a column temperature of 30° C. Typically, 5.0 μg of whole or digested protein was injected onto the column equilibrated in 5% B and a linear gradient from 5 to 85% B over 80 minutes was immediately initiated (A: 2% acetonitrile+0.1% acetic acid+0.020% TFA, B: 90% acetonitrile+0.1% acetic acid+0.018% TFA) The outlet from the HPLC UV detector was plumbed directly into a Finnigan LCQ Ion Trap Mass Spectrometer (Thermoquest Corp., San Jose, Calif.) with no flow splitting, a heated capillary temperature of 220° C., and a sheath gas flow of 75 (arbitrary units). The source voltage was 5.60 kV and the capillary voltage was 41.00 V. Mass spectra from 300–2000 m/z were recorded continuously during the gradient with 3 microscans per full scan. The most intense [M+2H]2+ ion in each spectrum was automatically selected by the LCQ for zoom scan and MSMS at 25% collision energy.

As described above, initial SDS-PAGE analysis of the non-reduced, affinity purified Zins1 NF revealed a series of bands between 15–20 kDa. Upon reduction of the protein, this series of bands shifts to 12–18 kDa and a new band appears with an apparent molecular weight of 4 kDa. While the non-reduced 15–20 kDa and reduced 12–18 kDa bands bind anti-FLAG antibody in a Western blot, the reduced 4 kDa band does not. N-terminal sequence analysis was carried out on bands excised from a PVDF blot of an 18% Tris-Glycine reducing SDS-PAGE gel, specifically, the bands at 4, 12, and 18 kDa. The two high molecular weight bands both gave single sequences beginning at the first residue of the FLAG sequence, Residue 1 (Asp; SEQ ID NO: 5), and both continued through the expected N-terminal sequence for Zins1 NF to residue 25 (Leu) of SEQ ID NO: 5 The 4 kDa band was >85% single sequence beginning at residue 100 (Ser) and continuing through the expected sequence to residue 122 (Leu) of SEQ ID NO: 5. The sequencing data corroborates the observed pattern in the Western blot with the upper molecular weight bands containing the FLAG sequence and the 4 kDa band containing no FLAG sequence. In addition the sequencing data indicates that Zins1 NF has been processed by the co-expressed PC3 at the expected C/A junction, cleaving the protein after the residues 96–99 (ArgLysLysArg) of SEQ ID NO: 5, to yield an A chain beginning at residue 100 (Ser) of SEQ ID NO: 5. Since the heterogeneity observed in the purified Zins1 NF is not due to differential processing of the polypeptide chain at the N-terminus or the C/A junction, it may be due to differential processing at the B/C junction or glycosylation events.

In order to ascertain if glycosylation is a factor in the observed heterogeneity, Zins1 NF was digested with PNGaseF and sialidase. Glycosidase PAGE analysis was performed as follows:

25 μg of protein was subjected to PNGaseF (peptide-N-glycosidase F) digestion. The protein was digested at 0.5 mg/ml protein. and 0.2 U/ml Oxford GlycoSystems (Rosedale, N.Y.) recombinant *F. meningosepticum* PNGaseF in 20 mM sodium phosphate+50 mM EDTA pH 7.5. The digest was incubated at 37° C. for 24 hrs. 5 μg of the treated protein was then analyzed by SDS-PAGE.

25 μg of protein was subjected to sialidase digestion. The protein was digested at 0.5 mg/ml protein and 4.0 U/ml Oxford GlycoSystems recombinant *C. perfringens* sialidase in 50 mM sodium acetate pH 5.0. The digest was incubated at 37° C. for 24 hrs. 5 μg of the treated protein was then analyzed by SDS-PAGE.

5 μg each of untreated, PNGaseF-treated, and sialidase-treated Zins1 NF was diluted with an equal volume of NOVEX 2× Tris-Glycine SDS sample buffer (NOVEX, San Diego, Calif.), boiled for 3–5 minutes, and loaded onto a NOVEX 18% Tris-Glycine gel. In addition, 5 μg each of untreated, PNGaseF-treated, and sialidase-treated Zins1 NF was diluted with an equal volume of NOVEX 2× Tris-Glycine SDS sample buffer (NOVEX, San Diego, Calif.) containing 5% b-mercaptoethanol, boiled for 3–5 minutes, and loaded onto a NOVEX 18% Tris-Glycine gel. Both the non-reduced and reduced gels were run at a constant voltage of 125V and visualized with Coomassie Blue staining. NOVEX Mark 12 Wide Range Protein Standards were used to determine apparent molecular weights.

Non-reducing and reducing SDS-PAGE analysis of the PNGaseF-treated Zins1 NF revealed no differences relative to the untreated material. Treatment of Zins1 NF with sialidase resulted in a shift of the upper molecular weight bands to 14–18 kDa in the non-reducing gel and 12–16 kDa in the reducing gel, an average loss of ~1–2 kDa in apparent molecular weight. The band at 4 kDa in the reducing gel was unaffected. The results of the glycosidase treatment indicates that the single potential N-glycosylation site present in Zins1 NF, AsnLeuSer, residues 73–75 of SEQ ID NO: 5, is not glycosylated. However, the sialidase results suggest that Zins1 NF is O-glycosylated with sialylated O-glycans and that these O-glycans are not located on the A chain.

Confirmation of the putative O-glycosylation was obtained via monosaccharide composition analysis. Monosaccharide composition for Zins1 was analyzed as follows: Monosaccharide composition was carried out on a Dionex system composed of a DX500 HPLC with an ED40 electrochemical detector, a GP40 pump, and a CARBOPAC-PA 10 column (Dionex, Sunnydale, Calif.). In both types of analyses, Dionex monosaccharide standards were used to calibrate the instrument. The glycoprotein fetuin was used as a positive control (Sigma. St. Louis, Mo.).

For sialic acid analysis, 2–8 μg of Zins1 NF was vacuum centrifuged to dryness without heat and reconstituted in 500 μl of 0.1 N TFA. After mixing the samples were incubated at 80° C. for 60 min., vacuum centrifuged to dryness without heat and reconstituted in 100 μl of distilled $H_2O$. 25 μl of hydrosylate was injected onto the Dionex system equilibrated in 50 mM sodium acetate/100 mM NaOH. A gradient to 180 mM sodium acetate/100 mM NaOH over 25 minutes was used. Triplicate analyses were averaged.

For neutral monosaccharide analysis, 2–8 μg of NF-zins1 was vacuum centrifuged to dryness without heat and reconstituted in 500 μl of 2.0 N TFA. After mixing the samples were incubated at 100° C. for 4 hours, vacuum centrifuged to dryness without heat and reconstituted in 100 μl of distilled $H_2O$. 25 μl of hydrosylate was injected onto the Dionex system equilibrated in 18 mM NaOH. An isocratic separation at 18 mM NaOH over 25 minutes was used. Triplicate analyses were averaged.

Sialic acid composition analysis showed that Zins1 NF has 6.0±0.5 moles of sialic acid per mole of protein and that these sialic acids are N-acetylneuraminic acid (NeuNAc) and not N-glycolylrneuraminic acid (NeuNGc) residues. Neutral monosaccharide composition analysis showed that NF-zins1 has 3.7±1.0 moles N-acetylgalactosamine (GalNAc) and 1.3±0.4 moles galactose (Gal) per mole of protein. These figures are consistent with an average of 2.7 disialylated mucin-type O-glycans (NeuNAcα2–3Galβ1–3 (NeuNAcα2–6)GalNAc-Ser/Thr) on each molecule of NF-zins1. No N-acetylglucosamine (GlcNAc) or fucose (Fuc) was detected and only a small amount of mannose (0.4±0.2 moles mannose per mole protein), consistent with a lack of N-glycans.

LCMS analysis of reduced Zins1 NF resulted in a very broad peak eluting from ~27–34 minutes with a sharp peak superimposed at 30.7 minutes. The broadness of the peak and the dearth of ions generated from it is typical of heterogeneous glycosylated proteins. One mass was discernible at 33.5 minutes, 12831.7 Da, a mass consistent with that expected for uncleaved B/C chain (Asp1-Arg99, residues 1 to 99 of SEQ ID NO: 5) with 2 disialylated mucin type O-glycans, 12834.2 Da. Presumably the material eluting before this mass is more heavily glycosylated (and thus more heterogeneous) B/C chain. The peptide eluting at 30.7 minutes ionized well and has a mass of 2789.5 Da, consistent with the expected molecular weight (2789.2 Da) of the predicted A chain, Ser100-Thr 124 (residues 100 to 124 of SEQ ID NO: 5.

LCMS and concurrent MSMS analysis of trypsinized native Zins1 NF revealed tryptic peptides from 89% of the complete sequence of Zins1 NF from Asp1 to Thr124. The tryptic peptides from the "C peptide" were not any less abundant than those from the "B chain" or A chain, suggesting that there is no B/C junction processing in Zins1 NF. A mass of 4289.5 Da was observed eluting at 29.4 minutes; the mass expected for Gly15-Arg19+His23-Lys33+His103-Thr124 (residues of SEQ ID NO: 5) joined by three disulfide bonds is 4289.0 Da. This observed mass is consistent with, though not exclusively, the disulfide bonding pattern expected from homology to the insulin family, i.e. Cys16-Cys110, Cys28-Cys123, and Cys109-Cys114 as shown in SEQ ID NO: 5. Furthermore, masses were observed that are consistent with tryptic peptide Thr34-Lys50 (as shown in SEQ ID NO: 5)+0–1 O-glycans (27.6 minutes), Glu51-Lys79 (as shown in SEQ ID NO: 5)+2–3 O glycans (29.5 minutes), and Asp60-Lys79 (as shown in SEQ ID NO: 5)+0–1 O-glycans (30.2–31.1 minutes).

The observed pattern of tryptic O-glycopeptides reveals that there are 4 O-glycosylation sites in the "C peptide" region of Zins1 NF. One site is contained in O-glycopeptide Thr34-Lys50 (as shown in SEQ ID NO: 5) and the modified residue is Thr34, Thr36, Thr37, Thr38, or Ser46 (as shown in SEQ ID NO: 5). Two sites are contained in O-glycopeptide Glu51-Lys59 (as shown in SEQ ID NO: 5) and the modified residues are Ser54, Thr55, and/or Ser56 (as shown in SEQ ID NO: 5). Finally, one site is contained in O-glycopeptide Asp60-Lys79 (as shown in SEQ ID NO: 5) and the modified residue is Thr66, Thr67, Ser68, or Ser75 (as shown in SEQ ID NO: 5).

Example 4

In Vitro Testing of Zins1 Protein

A. Isolation of Positive Control for Islet Proliferation Assay

To establish an assay to measure proliferation in islets in vitro, a positive control was isolated and characterized as fetal antigen 1 (FA1) as follows:

Pancreata from four 8–11 week old, p53–/– male mice (Taconic Farms, Germantown, N.Y.) were excised. The dissected pancreata were placed in a sterile 30 mm petri dish containing 7 ml of HBSS (Table 5)+5 mM $CaCl_2$, and the tissue was minced for exactly 2 minutes. Using a 10 ml pipet, the tissue was transferred to a sterile 25 ml screw-capped, round-bottom centrifuge tube, and 20 ml HBSS+5 mM $CaCl_2$, was added. After settling (about 2 minutes), the supernatant (containing fat and connective tissue) was removed. This procedure was repeated twice.

24 mg collagenase (Collagenase Type XI, Sigma Chemical Co., St. Louis, Mo.) was dissolved in 12 ml HBSS+5 mM $CaCl_2$ just prior to use, and was kept on ice. The collagenase solution (6 ml) was added to the minced tissue to a final concentration of 2 mg/ml. The cell mixture was placed on a shaker (300 rpm at 37° C.) for 15 minutes, and then quickly centrifuged for ~2 minute at 800 rpm in a Beckman CS-6R centrifuge with a swinging bucket rotor (Beckman Instruments, Palo Alto, Calif.). The supernatant was discarded.

6 ml fresh collagenase solution and 800 µl DNAse were added, and the cell mixture was returned to the shaker for up to 20 minutes. 50 µl of cell mixture sample was added to 150 µl DTZ (Table 6), and was examined using a dissecting microscope to ascertain when the islet cells were isolated, but not over-digested.

When the islet cells were isolated, the collagenase digestion was stopped by adding 15 ml HBSS+10% FBS to the mixture, and the mixture was then centrifuged in a Beckman CS-6R centrifuge with a swinging bucket rotor (Beckman Instruments, Palo Alto, Calif.) ~2 minutes at 800 rpm (the "wash step"). The supernatant was removed and discarded. The wash step was repeated two more times.

After washing, the cell pellet was resuspended in 2 ml HBSS, and the resuspended preparation was placed on two PERCOLL (Table 7) gradients (3 ml 40% PERCOLL and 3 ml 60% PERCOLL per 50 ml tube). One ml of this cell suspension was added to each tube. An additional 2 ml of HBSS was used to sequentially rinse the tubes from which the cell pellets were previously removed. This 2 ml of rinse suspension was added in 1 ml aliquots to each of the two gradients. Thus, each 50 ml tube had 2 ml of cell suspension on the top, then 3 ml of 40% PERCOLL, and finally 3 ml of 60% PERCOLL. The tubes were centrifuged in a Beckman CS-6R centrifuge with a swinging bucket rotor (Beckman Instruments) at 1850 rpm for 20 minutes, without the brake on.

After centrifugation, the top and bottom gradient interfaces were removed with a sterile transfer pipet, and each interface was transferred to a separate 50 ml tube. HBSS +10% FBS was added to the interface and washed by centrifugation in a Beckman CS-6R centrifuge with a swinging bucket rotor (Beckman Instruments) for 10 minutes at 925 rpm.

The top and bottom interfaces were filtered through a 70 µm nylon cell strainer (Becton Dickinson & Co., San Jose, Calif.). The islet cells remained on the filter, and exocrine tissue passed through. The filter was flipped upside-down in a 60 mm petri dish, and the islet cells were washed into the dish. To ensure their isolation from other tissue, the islet cells were plucked into a clean 60 mm non-tissue culture-treated dish containing RPMI growth medium (Table 8) +10% FBS. The islets were incubated at 37° C., 5% $CO_2$ and the medium was changed at 24 and 48 hours.

TABLE 5

HBSS 50 ml 10X HBSS
10 ml 1M Hepes
2.4 ml 7.5% $NaHCO_3$
5 ml PSN (100 × penicillin-streptomycin-neomycin)
Add sterile milli-Q water up to 500 ml and filter

TABLE 6

DTZ 10 mg DTZ (Sigma, St. Louis, MO)
1 ml DMSO, to dissolve DTZ
Make to 10 ml final volume with HBSS
Filter

TABLE 7

PERCOLL

90% : 90 ml 100% PERCOLL + 10 ml 10X HBSS
60% : 30 ml 90% PERCOLL + 15 ml HBSS
40% : 20 ml 90% PERCOLL + 25 ml HBSS

TABLE 8

RPMI 2.4 ml 7.5% NaHCO$_3$
10 ml 1M Hepes
5 ml 100 × PSN
5 ml 100 × Glutamine
RPMI-1640 (to a final volume of 450 ml)
50 ml fetal calf serum Islets, obtained as described above, were placed in a 60 mm petri dish in RPMI +10% FBS, and nine days later the whole islets were removed from the petri dish and replated in another 60 mm petri dish. Twenty one days later, the first dish was confluent, and the cells were removed with trypsin and passed into a T$_{25}$ flask.

Conditioned culture medium removed from these islet cells was added to cultures of normal BALB/c islets were isolated in MATRIGEL Basement Membrane Matrix (Collaborative Biomedical Products, Bedford, Mass.). The normal mouse islet phenotype changed, becoming huge with much branching and forming cyst-like structures. This conditioned medium was designated IDC53.1. Various other conditioned media obtained either from cultures of osteoclast, osteoblast or dendritic cells obtained from p53−/− knockout mice (see WO 9607733), or from cultures of normal C57/Black 6 islet cells, did not exhibit this activity. In addition, normal BALB/c islets placed in this conditioned medium developed "cobblestone" cells all around the islet. This effect was not seen when various other conditioned media were tested.

A BrdU incorporation study using BALB/c islets incubated with IDC53.1 conditioned medium (CM) was performed, to test whether there were cells within the islets that were proliferating. Briefly, one group of four T$_{12.5}$ flasks (Becton Dickinson) was inoculated with 100 islets each, and 5×IDC53.1 CM+0.5% FBS was added to each flask. Another group of three T$_{12.5}$ flasks was inoculated with 100 islets each, and SFIF medium (serum free/insulin free medium; Becton Dickinson) +0.5% FBS was added.

BrdU (Becton Dickinson) was added to the islet cell cultures daily, to a final concentration of 10 μM. A flask from each group was harvested on days 4, 8 and 12. On day 8, two of the four flasks in the IDC53.1 CM test group were harvested. One of these flasks was used for an isotype control. The protocol and reagents for BrdU assay are available from Becton Dickinson Immunocytometry Systems, San Jose, Calif., and were used according to the manufacturer's specifications.

For each harvested flask, the islets were harvested, washed twice in 1% BSA/PBS, and centrifuged at 800 rpm for 10 minutes. The pellet was resuspended in 200 μl of 1×PBS on ice. Islets were slowly added to 2.5 ml cold 70% ethanol in a siliconized glass tube while maintaining a vortex. The islets were incubated on ice for 30 minutes, and the result was fixed islet cells. The fixed islets were centrifuged at 1000 rpm for 10 minutes at 10° C., and the ethanol was carefully removed.

One ml of 2 N HCl/Triton X-100 was slowly added to the cells, a few drops at a time, while maintaining a vortex. The mixture was incubated at room temperature for 30 minutes, to denature the DNA and produce single-stranded molecules. The preparation was centrifuged at 1000 rpm for 10 minutes, and then the supernatant was removed and the pellet resuspended in 1 ml of 0.1 M Na$_2$B$_4$O$_7$.10 H$_2$O, pH 8.5, to neutralize the acid. The resultant cells may be stored at this point by centrifuging, resuspending in cold 70% ethanol, and storing at −20° C.

The cells are then centrifuged at 1000 rpm for 10 minutes, washed with 1 ml of 0.5% TWEEN 20 in 1% BSA/PBS (TWEEN/BSA/PBS), and resuspended in 100 μl TWEEN/BSA/PBS. To this resuspended preparation was added 20 μl of FITC-labeled anti-BrdU antibody or isotype control. The mixture was incubated overnight on a shaker at 4° C. for whole islets. Thereafter, the cells were washed 3 times using 1 ml TWEEN/BSA/PBS, where each wash was performed for at least 2 hours on the shaker. Preferable, the final wash is left overnight.

The islet preparation was then mounted on glass slides with depressions to prevent the islets from losing their shape. FLUOROGUARD Antifade Reagent (BioRad, Hercules, Calif.) was the mounting medium used. All positive BrdU cells per islet were counted for each of the three harvest days. On Day 4, there were 1.5 times more positive cells in the islets cultured in the 5×IDC53.1 CM than in the control. On Day 8, there were 2.9 times more positive cells, and on Day 12 there were 3.5 times more positive cells, as compared to the control.

Islets were prepared as described above for a BrdU assay, but after incubation with the BrdU, the islets were harvested, fixed, embedded, sliced and stained for anti-Brdu, anti-insulin, anti-glucagon and anti-somatastatin using standard immunohistochemistry techniques. The positive BrdU cells were also positive for insulin, and were negative for glucagon and somatostatin, strongly suggesting that the cells are β-cells.

Using standard immunodepletion methods, it was demonstrated that FA1 was a factor in islet proliferation, and useful as a positive control for testing islet proliferation.

B. Zins1 Testing in In Vitro Islet Assay

Normal BALB/c islets were isolated from 8.5 week old male mice. The islets were plated into a 96-well flat bottom plate, with approximately 15 islets/well in serum-free/insulin-free +0.5w FCS medium, in duplicate. Zins1 diluted serum-free/insulin-free +0.5% FCS medium was added at concentrations of 1–20 ng/ml, along with a negative control of serum-free/insulin-free +0.5% FCS medium, and a positive control of conditioned medium as described in A.

At day 5, the wells to which positive control and all concentrations of Zins1 had been added, cells were proliferating, with optimal growth in the 1–10 ng/ml doses. At day 8, the 1–10 ng/ml dose range of Zins1clearly contained adherent cells that appeared to be growing from the islets. The cells which grew out of islets treated with Zins1 exhibited a spindle morphology in contrast to the FA-1 treated islets, which yielded cobblestone monolayers. Islets treated only with basal medium had no cell outgrowth and appeared senescent.

These data show that Zins1 can maintain islets in a viable condition and further stimulate expansion of specific cell types by outgrowth from the islets.

From the foregoing, it will be appreciated that, although specific embodiments of the invention have been described herein for purposes of illustration, various modifications may be made without deviating from the spirit and scope of the invention.

We claim:

1. An isolated protein produced by a method comprising:

culturing a host cell into which has been introduced a DNA expression vector comprising the following operably linked elements:
    a transcription promoter;
    a DNA segment comprising a nucleotide sequence shown in SEQ ID NO: 1 from nucleotide 76 to nucleotide 417; and
    a transcription terminator, wherein said host cell expresses the polypeptide encoded by said DNA segment; and
recovering said protein.

2. The protein of claim 1, wherein the host cell is a mammalian cell.

3. The protein of claim 1, wherein the host cell has had a second DNA vector introduced into it, wherein said second expression vector comprises the following operably linked elements:
    a transcription promoter;
    a DNA segment encoding an endoprotease; and
    a transcription terminator, wherein said host cell expresses the polypeptide encoded by the DNA segment consisting of a nucleotide sequence shown in SEQ ID NO: 1 from nucleotide 76 to nuclcotide 417; and said DNA segment encoding said endoprotease.

\* \* \* \* \*

UNITED STATES PATENT AND TRADEMARK OFFICE
CERTIFICATE OF CORRECTION

PATENT NO. : 6,737,509 B1
DATED : May 18, 2004
INVENTOR(S) : Stephen R. Jaspers et al.

It is certified that error appears in the above-identified patent and that said Letters Patent is hereby corrected as shown below:

Title page,
Item [54] Title, replace "ZINSI" with -- ZINS1 --.

Signed and Sealed this

Seventh Day of June, 2005

JON W. DUDAS
*Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 420 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: Coding Sequence
       (B) LOCATION: 1...417
       (D) OTHER INFORMATION:

(xi) SEQUENCE DESCRIPTION: SEQ ID NO:1:

```
ATG GCC AGC CTG TTC CGG TCC TAT CTG CCA GCA ATC TGG CTG CTG CTG      48
Met Ala Ser Leu Phe Arg Ser Tyr Leu Pro Ala Ile Trp Leu Leu Leu
 1               5                  10                  15

AGC CAA CTC CTT AGA GAA AGC CTA GCA GCA GAG CTG AGG GGA TGT GGT      96
Ser Gln Leu Leu Arg Glu Ser Leu Ala Ala Glu Leu Arg Gly Cys Gly
                20                  25                  30

CCC CGA TTT GGA AAA CAC TTG CTG TCA TAT TGC CCC ATG CCT GAG AAG     144
Pro Arg Phe Gly Lys His Leu Leu Ser Tyr Cys Pro Met Pro Glu Lys
            35                  40                  45

ACA TTC ACC ACC ACC CCA GGA GGG TGG CTG CTG GAA TCT GGA CGT CCC     192
Thr Phe Thr Thr Thr Pro Gly Gly Trp Leu Leu Glu Ser Gly Arg Pro
 50                  55                  60

AAA GAA ATG GTG TCA ACC TCC AAC AAC AAA GAT GGA CAA GCC TTA GGT     240
Lys Glu Met Val Ser Thr Ser Asn Asn Lys Asp Gly Gln Ala Leu Gly
 65                  70                  75                  80

ACG ACA TCA GAA TTC ATT CCT AAT TTG TCA CCA GAG CTG AAG AAA CCA     288
Thr Thr Ser Glu Phe Ile Pro Asn Leu Ser Pro Glu Leu Lys Lys Pro
                85                  90                  95

CTG TCT GAA GGG CAG CCA TCA TTG AAG AAA ATA ATA CTT TCC CGC AAA     336
Leu Ser Glu Gly Gln Pro Ser Leu Lys Lys Ile Ile Leu Ser Arg Lys
            100                 105                 110

AAG AGA AGT GGA CGT CAC AGA TTT GAT CCA TTC TGT TGT GAA GTA ATT     384
Lys Arg Ser Gly Arg His Arg Phe Asp Pro Phe Cys Cys Glu Val Ile
        115                 120                 125

TGT GAC GAT GGA ACT TCA GTT AAA TTA TGT ACA TAG                     420
Cys Asp Asp Gly Thr Ser Val Lys Leu Cys Thr
    130                 135
```

(2) INFORMATION FOR SEQ ID NO:2:

(i) SEQUENCE CHARACTERISTICS:
       (A) LENGTH: 139 amino acids
       (B) TYPE: amino acid
       (C) STRANDEDNESS: single
       (D) TOPOLOGY: linear (ii) MOLECULE TYPE: protein (v) FRAGMENT TYPE: internal (xi) SEQUENCE DESCRIPTION: SEQ ID NO:2:

```
Met Ala Ser Leu Phe Arg Ser Tyr Leu Pro Ala Ile Trp Leu Leu Leu
 1               5                  10                  15
```

```
Ser Gln Leu Leu Arg Glu Ser Leu Ala Ala Glu Leu Arg Gly Cys Gly
         20                  25                  30

Pro Arg Phe Gly Lys His Leu Leu Ser Tyr Cys Pro Met Pro Glu Lys
             35                  40                  45

Thr Phe Thr Thr Thr Pro Gly Gly Trp Leu Leu Glu Ser Gly Arg Pro
 50                  55                  60

Lys Glu Met Val Ser Thr Ser Asn Asn Lys Asp Gly Gln Ala Leu Gly
 65                  70                  75                  80

Thr Thr Ser Glu Phe Ile Pro Asn Leu Ser Pro Glu Leu Lys Lys Pro
                 85                  90                  95

Leu Ser Glu Gly Gln Pro Ser Leu Lys Lys Ile Ile Leu Ser Arg Lys
             100                 105                 110

Lys Arg Ser Gly Arg His Arg Phe Asp Pro Phe Cys Cys Glu Val Ile
             115                 120                 125

Cys Asp Asp Gly Thr Ser Val Lys Leu Cys Thr
             130                 135
```

(2) INFORMATION FOR SEQ ID NO:3:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 1...477
        (D) OTHER INFORMATION:

(xi) SEQUENCE DESCRIPTION: SEQ ID NO:3:

```
ATG GAT GCA ATG AAG AGA GGG CTC TGC TGT GTG CTG CTG CTG TGT GGC      48
Met Asp Ala Met Lys Arg Gly Leu Cys Cys Val Leu Leu Leu Cys Gly
 1               5                  10                  15

GCC GTC TTC GTT TCG CCC AGC CAG GAA ATC CAT GCC GAG TTC CAG AGA      96
Ala Val Phe Val Ser Pro Ser Gln Glu Ile His Ala Glu Phe Gln Arg
                 20                  25                  30

GGA CGC AGA CAT CAC CAT CAC CAT CAC GGT GGC TCC GGA GCA GAG CTG     144
Gly Arg Arg His His His His His His Gly Gly Ser Gly Ala Glu Leu
             35                  40                  45

AGG GGA TGT GGT CCC CGA TTT GGA AAA CAC TTG CTG TCA TAT TGC CCC     192
Arg Gly Cys Gly Pro Arg Phe Gly Lys His Leu Leu Ser Tyr Cys Pro
 50                  55                  60

ATG CCT GAG AAG ACA TTC ACC ACC ACC CCA GGA GGG TGG CTG CTG GAA     240
Met Pro Glu Lys Thr Phe Thr Thr Thr Pro Gly Gly Trp Leu Leu Glu
 65                  70                  75                  80

TCT GGA CGT CCC AAA GAA ATG GTG TCA ACC TCC AAC AAC AAA GAT GGA     288
Ser Gly Arg Pro Lys Glu Met Val Ser Thr Ser Asn Asn Lys Asp Gly
                 85                  90                  95

CAA GCC TTA GGT ACG ACA TCA GAA TTC ATT CCT AAT TTG TCA CCA GAG     336
Gln Ala Leu Gly Thr Thr Ser Glu Phe Ile Pro Asn Leu Ser Pro Glu
             100                 105                 110

CTG AAG AAA CCA CTG TCT GAA GGG CAG CCA TCA TTG AAG AAA ATA ATA     384
Leu Lys Lys Pro Leu Ser Glu Gly Gln Pro Ser Leu Lys Lys Ile Ile
             115                 120                 125

CTT TCC CGC AAA AAG AGA AGT GGA CGT CAC AGA TTT GAT CCA TTC TGT     432
Leu Ser Arg Lys Lys Arg Ser Gly Arg His Arg Phe Asp Pro Phe Cys
             130                 135                 140

TGT GAA GTA ATT TGT GAC GAT GGA ACT TCA GTT AAA TTA TGT ACA TAG     480
Cys Glu Val Ile Cys Asp Asp Gly Thr Ser Val Lys Leu Cys Thr
```

```
Cys Glu Val Ile Cys Asp Asp Gly Thr Ser Val Lys Leu Cys Thr
145                 150                 155
```

(2) INFORMATION FOR SEQ ID NO:4:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Glu Phe Gln Arg
                20                  25                  30

Gly Arg Arg His His His His His His Gly Gly Ser Gly Ala Glu Leu
            35                  40                  45

Arg Gly Cys Gly Pro Arg Phe Gly Lys His Leu Leu Ser Tyr Cys Pro
    50                  55                  60

Met Pro Glu Lys Thr Phe Thr Thr Thr Pro Gly Gly Trp Leu Leu Glu
65                  70                  75                  80

Ser Gly Arg Pro Lys Glu Met Val Ser Thr Ser Asn Asn Lys Asp Gly
                85                  90                  95

Gln Ala Leu Gly Thr Thr Ser Glu Phe Ile Pro Asn Leu Ser Pro Glu
                100                 105                 110

Leu Lys Lys Pro Leu Ser Glu Gly Gln Pro Ser Leu Lys Lys Ile Ile
            115                 120                 125

Leu Ser Arg Lys Lys Arg Ser Gly Arg His Arg Phe Asp Pro Phe Cys
    130                 135                 140

Cys Glu Val Ile Cys Asp Asp Gly Thr Ser Val Lys Leu Cys Thr
145                 150                 155
```

(2) INFORMATION FOR SEQ ID NO:5:

(i) SEQUENCE CHARACTERISTICS:
        (A) LENGTH: 124 amino acids
        (B) TYPE: amino acid
        (C) STRANDEDNESS: single
        (D) TOPOLOGY: linear (xi) SEQUENCE DESCRIPTION: SEQ ID NO:5:

```
Asp Tyr Lys Asp Asp Asp Lys Gly Ser Ala Glu Leu Arg Gly Cys
1               5                   10                  15

Gly Pro Arg Phe Gly Lys His Leu Leu Ser Tyr Cys Pro Met Pro Glu
                20                  25                  30

Lys Thr Phe Thr Thr Thr Pro Gly Gly Trp Leu Leu Glu Ser Gly Arg
            35                  40                  45

Pro Lys Glu Met Val Ser Thr Ser Asn Asn Lys Asp Gly Gln Ala Leu
    50                  55                  60

Gly Thr Thr Ser Glu Phe Ile Pro Asn Leu Ser Pro Glu Leu Lys Lys
65                  70                  75                  80

Pro Leu Ser Glu Gly Gln Pro Ser Leu Lys Lys Ile Ile Leu Ser Arg
                85                  90                  95

Lys Lys Arg Ser Gly Arg His Arg Phe Asp Pro Phe Cys Cys Glu Val
                100                 105                 110
```

```
Ile Cys Asp Asp Gly Thr Ser Val Lys Leu Cys Thr
        115                 120
```

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 4...13
        (D) OTHER INFORMATION: Xaa is any amino acid except Cys (xi) SEQUENCE DESCRIPTION: SEQ ID NO:6:

```
Leu Cys Gly Xaa Xaa Xaa Xaa Xaa Xaa Xaa Xaa Xaa Xaa Cys
 1           5                       10
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...5
        (D) OTHER INFORMATION: Xaa is any amino acid except Cys
        (A) NAME/KEY: Other
        (B) LOCATION: 7...14
        (D) OTHER INFORMATION: Xaa is any amino acid except Cys (xi) SEQUENCE DESCRIPTION: SEQ ID NO:7:

```
Cys Cys Xaa Xaa Xaa Cys Xaa Xaa Xaa Xaa Xaa Xaa Xaa Xaa Cys
 1           5                       10                  15
```